US012327632B2

(12) United States Patent
Bindszus et al.

(10) Patent No.: US 12,327,632 B2
(45) Date of Patent: Jun. 10, 2025

(54) AUTOMATIC PATIENT RECORD UPDATING

(71) Applicant: KONINKLIJKE PHILIPS N.V., Eindhoven (NL)

(72) Inventors: Andreas Bindszus, Boeblingen (DE); Sabine Funke-Schaeff, Aidlingen (DE); Harald Greiner, Nufringen (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 555 days.

(21) Appl. No.: 17/039,727

(22) Filed: Sep. 30, 2020

(65) Prior Publication Data

US 2021/0098094 A1 Apr. 1, 2021

(30) Foreign Application Priority Data

Sep. 30, 2019 (EP) .................................... 19200399

(51) Int. Cl.
| | |
|---|---|
| *A61B 5/00* | (2006.01) |
| *G06F 18/22* | (2023.01) |
| *G16H 10/60* | (2018.01) |
| *G16H 15/00* | (2018.01) |
| *G16H 40/67* | (2018.01) |

(52) U.S. Cl.
CPC ............. *G16H 40/67* (2018.01); *G06F 18/22* (2023.01); *G16H 10/60* (2018.01); *G16H 15/00* (2018.01)

(58) Field of Classification Search
CPC ........ G16H 40/67; G16H 10/60; G16H 15/00; G16H 30/20; G06F 18/22
See application file for complete search history.

(56) References Cited

U.S. PATENT DOCUMENTS

| | | | |
|---|---|---|---|
| 9,082,038 B2 | 7/2015 | Kozitsky | |
| 9,508,009 B2 | 11/2016 | Wnuk | |
| 2004/0103367 A1 | 5/2004 | Riss | |
| 2004/0128613 A1 | 7/2004 | Sinisi | |
| 2014/0098209 A1 | 4/2014 | Neff | |
| 2015/0005650 A1* | 1/2015 | Banet | A61B 5/349 |
| | | | 600/509 |
| 2016/0019345 A1 | 1/2016 | Peguero | |
| 2017/0238842 A1* | 8/2017 | Jacquel | A61B 5/14542 |
| 2020/0250406 A1* | 8/2020 | Wang | H04N 23/80 |

FOREIGN PATENT DOCUMENTS

WO 2019154744 A1 8/2019

OTHER PUBLICATIONS

"How to Improve your Business with OCR Software", Jul. 18, 2018.

\* cited by examiner

*Primary Examiner* — Maroun P Kanaan (57) ABSTRACT

The present invention is concerned with the automated updating of a digital patient record with actual vital signs data values for the patient, thereby obviating the need for a healthcare professional attending to the patient to manually input such data values into the digital patient record. To this end, the present application provides several computer-implemented methods for capturing such vital signs data values in digital form, e.g. a photographic image or screen capture$_{[BA1]}$, and automatically extracting the vital signs data values captured in such a digital image therefrom, e.g. using OCR algorithms. Also provided are computer program products for implementing such methods and electronic devices configured to implement such methods.

20 Claims, 7 Drawing Sheets

AUTOMATIC PATIENT RECORD UPDATING

FIELD OF THE INVENTION

The present invention relates to a computer-implemented method of updating a patient record in a medical database with a processor arrangement of an electronic device.

The present invention further relates to a computer-implemented method of generating an image of a display screen of a patient monitoring system displaying at least one vital signs data value of a patient being monitored by said patient monitoring system with a processor arrangement of an electronic client device.

The present invention further relates to a computer program product for implementing such methods on an electronic device.

The present invention further relates to an electronic device arranged to implement the method of updating a patient record in a medical database.

The present invention further relates to an electronic client device arranged to implement the method of generating an image of a display screen of a patient monitoring system displaying at least one vital signs data value of a patient being monitored by said patient monitoring system.

BACKGROUND OF THE INVENTION

It is of paramount importance that patients in clinical care, e.g. hospitalized patients, are closely monitored by healthcare professionals such that any detrimental changes to the health of such patients can timely be discovered. To this end, such healthcare professionals typically utilize a plethora of electronic devices to keep up to date with the medical status of their patients. For example, the patient may be permanently or regularly connected to a patient monitoring system that monitors vital signs of the patient, such as for example body temperature, blood pressure, heart rate, (arterial) oxygen saturation, blood glucose levels, and so on. The healthcare professional in turn may be utilizing a portable electronic device giving the healthcare professional direct access to the patient's medical record, such that the healthcare professional can easily access the up to date medical information of the patient, for example when consulting with the patient. Such a portable electronic device may be a dedicated electronic device or a generic electronic device such as a smartphone or tablet computer onto which a software program (app) is installed through which the healthcare professional can access to the patient's medical record.

In order to keep the patient's medical record up to date, it is typically required that this medical record is periodically updated with vital signs information acquired with the patient monitoring system. Where the patient monitoring system is not integrated with the medical records database (as typically is the case), it is required that the healthcare professional updates the patient's medical record, e.g. upon visiting the patient. Such updates may, in addition to the vital signs data values, further include an up to date score expressing (a change in) the medical condition of the patient such as an Early Warning Score (EWS), an AVPU score, and so on. This however is cumbersome and time-consuming. Moreover, the manual input of vital signs data values into the patient's medical record as derived from the display screen of a patient monitoring system is subject to user error, especially when the healthcare professional is stretched in terms of workload. Hence, there is a need for a more efficient and reliable way of updating a patient record with such vital signs information.

SUMMARY OF THE INVENTION

The present invention seeks to provide a computer-implemented method of updating a patient record in a medical database with a processor arrangement of an electronic device to facilitate a more efficient and reliable way of updating such a patient record.

The present invention further relates to a computer-implemented method of generating an image of a display screen of a patient monitoring system displaying at least one vital signs data value of a patient being monitored by said patient monitoring system with a processor arrangement of an electronic client device to facilitate a more efficient and reliable way of updating the patient record of such a patient.

The present invention further relates to a computer program product for implementing such methods on an electronic device.

The present invention further relates to an electronic device arranged to implement the method of updating a patient record in a medical database.

The present invention further relates to an electronic client device arranged to implement the method of generating an image of a display screen of a patient monitoring system displaying at least one vital signs data value of a patient being monitored by the patient monitoring system.

According to an aspect, there is provided a computer-implemented method of updating a patient record in a medical database, the method comprising, with a processor arrangement of an electronic device, receiving an image of a display screen of a patient monitoring system displaying at least one vital signs data value of said patient; evaluating at least one region of interest of said image comprising one of said vital signs data values to extract said one vital signs data value from said image; updating the patient record with the extracted at least one vital signs data value; and storing the image in a database such that the image is associated with the updated patient record.

The present invention is based on the insight that the vital signs data values as captured by a patient monitoring system monitoring a patient may be captured from an image of the display screen of such a patient monitoring system using data capturing algorithms such as optical character recognition algorithms such that the vital signs data values may be acquired automatically rather than having to be input manually by healthcare professional such as a nurse or a consultant. In addition, by storing the captured image as well as the extracted vital signs data values, it can be verified if the extracted vital signs data values were correctly extracted from the image of the display screen of the patient monitoring system, which for instance may be useful if a healthcare professional evaluating the patient record has reason to believe some of the data in this record may be unreliable, e.g. physiologically impossible. The image in a first set of embodiments may be at least one photographic image of the display screen of the patient monitoring system, or alternatively give a second set of embodiments may be a screen capture of the display screen of the patient monitoring system. In case of the image being at least one photographic image, the image may be a single photographic image or a (video) stream or temporal sequence of photographic images. The latter for example may be useful where changes in the vital signs data values of the patient are to be captured. The second set of embodiments for example may be useful if an electronic client device operated by the healthcare professional such as a smart phone or tablet computer temporarily becomes part of the patient monitoring system, for example by establishing a communication link between the electronic client device and the patient monitor upon the healthcare professional examining or otherwise determining the physical condition of the patient, such that the vital signs information of the patient as required by the patient monitor may be displayed on the display screen of the electronic client device, e.g. within an app running on the electronic client device. In such scenarios, it may not be necessary to capture one or more photographic images of the display screen but instead a screen capture may be made in order to capture the displayed vital signs information.

It shall be understood by the person skilled in the art that the medical database and the database, wherein the image is stored, could be the same database or two separate ones with appropriate links between the patient records. An advantage of separating the two databases might be a flexibility in managing data storage as well as a workflow for medical data review. Some of the medical database providers might not allow an easy implementation of the image storage, therefore having a separate database for said storage linked to the medical database might enable a quick upgrade of the existing installed base of the medical databases. Further, it might be beneficial to keep the storage resources of the image data base (the database wherein the image is stored) limited and have the stored images reviewed by a medical practitioner during a predefined period of time after which all reviewed images can be deleted.

In an embodiment, the computer-implemented method further comprises generating an indicator value of an actual physical state of said patient from the extracted at least one vital signs data value and updating the patient record with the generated indicator value. For example, such an indicator value may be an early warning score (EWS) for said patient.

The computer-implemented method may further comprise displaying the extracted at least one vital signs data value on a display device to a user; receiving a verification command from said user; and updating the patient record with the extracted at least one vital signs data value and storing the image in the medical database and or the image database in response to the received verification command. This ensures that only vital signs data values approved by the user are stored in the patient record.

In a first set of embodiments, the one or more vital signs data values may be extracted from the image based on prior knowledge of where within the image particular vital signs data values are expected, as will be explained in further detail below. This typically will be the case in scenarios in which it is well-known which patient monitoring systems are in use within the clinical care environment such that it is possible to preconfigure the electronic device evaluating the captured image of the display screen of such a patient monitoring system such that the processor arrangement of the electronic device knows where to expect particular vital signs data values, e.g. a blood pressure value, a heart rate value, an oxygen saturation value, a body temperature value, and so on. However, in an alternative set of embodiments, evaluating said image to extract the vital signs data value from a region of interest in said image may comprise identifying a region of interest comprising a vital signs data value in said image; extracting the vital signs data value from the identified region of interest; matching the extracted vital signs data value to a particular vital sign of the patient by comparing said vital signs data value against a library of expectation values of data values for different vital signs; and updating a vital signs record of a vital sign in the patient record matched to the extracted vital signs data value with said extracted vital signs data value. This has the advantage that the electronic device does not have to rely on such prior knowledge of what vital signs data values are to be expected in particular regions of the captured image under evaluation as the electronic device is instead configured to predict to which particular vital sign an extracted data value is likely to belong based on the actual value of said data value.

In a preferred embodiment, the computer-implemented method further comprises receiving identification information of a person responsible for generating said image and associating at least one of the stored at least one vital signs data value and the stored image with the received identification information. This for instance can be used to establish responsibility for the uploading of particular images and vital signs data values extracted from such images into the patient record. This for example may be used to establish if a certain healthcare professional requires further training because the particular healthcare professional has been responsible for uploading incorrectly recognized vital signs data values of a patient. This is particularly relevant in embodiments in which the data extraction from such an image is performed on the same electronic device as the electronic device with which the image has been captured, e.g. the electronic client device of the healthcare professional, as in such a scenario the healthcare professional may be required to approve the vital signs data values extracted from the captured image before the patient record is updated with the extracted vital signs data values in order to further reduce the risk of incorrect data being entered into the patient record. In other words, in such a scenario the computer-implemented method may only update the patient record with the extracted vital signs data values upon receiving a user confirmation command indicative of the accuracy of the extracted vital signs data values. However, where such a command is given without justification, e.g. because of a discrepancy between the actual vital signs data values displayed on the display screen and the vital signs data values extracted by the electronic device, not only is it possible to determine this discrepancy because of the storage of the captured image together with the vital signs data values extracted from his image, but is also possible to determine who was responsible for allowing such incorrect data to be entered into the patient record by associating the stored vital signs data values and/or the stored image with the identification information of this person.

In accordance with another aspect, there is provided a computer-implemented method of generating at least one photographic image of a display screen of a patient monitoring system displaying at least one vital signs data value of a patient being monitored by said patient monitoring system with an electronic client device adapted to access a patient record of said patient, the electronic client device comprising a processor arrangement, a camera communicatively coupled to said processor arrangement, a display screen communicatively coupled to said processor arrangement and a data storage device storing a mask for aligning with a region of interest of the display screen of the patient monitoring system, the method comprising retrieving the mask for aligning with the region of interest of the display screen of the patient monitoring system from the data storage device; displaying said mask on the display screen of the electronic client device as an overlay over a view of the display screen of the patient monitoring device through said camera to facilitate aligning said view with said mask by a user of the electronic client device; receiving a capturing command for capturing at least one photographic image of said aligned view with said camera; and providing the captured at least one photographic image to a processor arrangement adapted to update said patient record in accordance with the method of any of the herein described embodiments.

The provision of such a mask configured in accordance with the screen layout of the display screen of the patient monitoring system can be advantageously used to generate the image such that the image correctly positions the one or more vital signs data values of the patient as displayed on the display screen of the patient monitoring system by a user of the electronic client device aligning the mask with the image is displayed on the display screen of the electronic client device. This ensures that the likelihood of the correct extraction of the one or more vital signs data values from the captured image is optimized.

In an embodiment, said mask forms part of a library of masks corresponding to respective regions of interest of the display screens of different patient monitoring systems stored in the data storage device, the method further comprising receiving a user input identifying the patient monitoring system; and selecting the mask corresponding to the identified patient monitoring system from said library based on the received user input. This for example is advantageous in scenarios in which multiple patient monitoring systems may be in use within the clinical care environment such that the provision of the library of masks allows a user of the electronic client device to select the appropriate mask from the library of masks to ensure that the patient's vital signs data values as displayed on the display screen of a particular patient monitoring system can be captured.

In an alternative embodiment, said mask forms part of a library of masks corresponding to respective regions of interest of the display screens of different patient monitoring systems stored in the data storage device, the method further comprising capturing an identification image of the patient monitoring system with the camera; identifying the patient monitoring system from said captured identification image; and selecting the mask corresponding to the identified patient monitoring system from said library. In this manner, the mask may be automatically selected from the library without requiring user intervention, which may reduce the risk of incorrect mask selection as well as further improve the ease of use of the electronic client device by the healthcare professional.

Such a mask may comprise a plurality of visible sectors, each sector corresponding to a region of interest including a particular vital signs data field on the display screen of the patient monitoring system. This further assists the healthcare professional in aligning the screen view of the image to be captured, as the visible sectors may be overlaid with the corresponding regions of interest of the display screen of the patient monitoring system in the screen view of the image to be captured on the electronic client device.

In an embodiment, the computer-implemented method further comprises executing at least part of any herein described embodiments of the computer-implemented method of updating the patient record of the patient as herein described on the processor arrangement of the electronic client device. In other words, the capture of the image of the display screen of the patient monitoring system with the electronic client device and a data extraction from the captured image may be performed on different electronic devices, e.g. the data extraction part may be performed on a server hosting the database holding the medical records of the patients registered with the clinical care environment, which for instance may be beneficial in terms of reducing the processing load of the electronic client device in order to avoid delays at the bedside of the patient. However, a drawback of this scenario is that verification of the data extracted from the captured image prior to uploading the data into the patient record is not straightforward as it would require the remote electronic device performing the data extraction of the image to return the image and data extracted from the image to the electronic client device for verification by its user. Therefore, it may be advantageous to have at least part of the computer-implemented method of automatically updating the patient record with vital signs data values extracted from the captured image as previously described executed by the processor arrangement of the electronic client device, e.g. to allow immediate verification of the extracted data values by the user of the electronic client device prior to uploading the extracted data values in the patient record as previously explained.

According to yet another aspect, there is provided a computer program product comprising a computer readable storage medium having computer readable program instructions embodied therewith for, when executed on a processor arrangement of an electronic device, cause the processor arrangement to implement the method of any of the herein described embodiments. Such a computer program product, e.g. an app stored on an app server or the like, may be used to configure an electronic device, e.g. a server or an electronic client device such as a smart phone or tablet computer to implement one or more embodiments of the methods of the present invention.

According to yet another aspect, there is provided an electronic device comprising a processor arrangement adapted to execute the herein described method of updating a patient record in a medical database. To this end, the electronic device for example may comprise the aforementioned computer program product.

According to yet another aspect, there is provided an electronic client device comprising a processor arrangement, a camera communicatively coupled to said processor arrangement, a display screen communicatively coupled to said processor arrangement and a data storage device for storing a mask for aligning with a region of interest of the display screen of a patient monitoring system, wherein the processor arrangement is adapted to execute the method of generating a screen capture of a display screen of a patient monitoring system displaying at least one vital signs data value of a patient being monitored by said patient monitoring system. To this end, the electronic client device for example may comprise the aforementioned computer program product.

BRIEF DESCRIPTION OF THE DRAWINGS

Embodiments of the invention are described in more detail and by way of non-limiting examples with reference to the accompanying drawings, wherein.

DETAILED DESCRIPTION OF THE EMBODIMENTS

It should be understood that the Figures are merely schematic and are not drawn to scale. It should also be understood that the same reference numerals are used throughout the Figures to indicate the same or similar parts.

Figure 1:
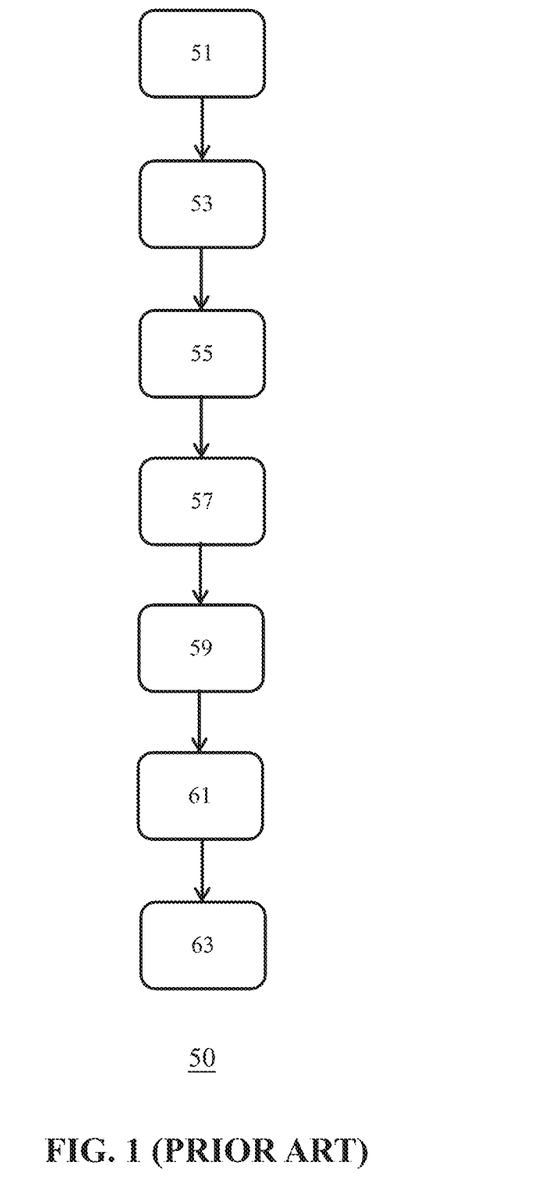
FIG. 1 schematically depicts a flow chart of a typical workflow of a healthcare professional when attending to a patient.

FIG. 1 is a flowchart of a typical procedure or workflow 50 undertaken by a healthcare professional such as a nurse or a consultant when checking the physical condition of a patient, e.g. within a clinical care environment such as a hospital. Such a healthcare professional may use an electronic client device such as a smart phone or tablet computer to interface with a database holding the patient records of the patients within the clinical care environment. For example, the electronic client device may have a software program such as an app installed that gives the healthcare professional access to such patient records. For example, such an app may allow the healthcare professional to evaluate the patient's medical history, e.g. a history of vital signs data values acquired over time for the patient, visualize trends in such data, e.g. in the shape of graphs or the like, and make changes to the patient record, e.g. by updating vital signs data values. The workflow 50 starts in operation 51, e.g. by launching the app, after which the healthcare professional provides identification information in operation 53. For example, the healthcare professional logs into the app by entering user credentials, which may be done manually or with the aid of a device such as a barcode scanner or the like with which an identification badge or the like of the healthcare professional is scanned in order to retrieve the identification information.

In operation 55, the patient is identified, for example through scanning a wristband or bracelet or the like worn by the patient, in order to access the appropriate patient record from a database storing a plurality of such patient records. In operation 57, the patient may be hooked up to a patient monitoring system for monitoring vital signs of the patient if the patient is not already hooked up to such a system and the vital signs data values determined in this manner are registered by the healthcare professional, e.g. by manually entering these vital signs data values in the patient record through the app. The healthcare professional may supplement these vital signs data values with observational information such as for example AVPU observations, which may be used in a calculation of a score indicative of the actual physical state of the patient such as an EWS in operation 61. Finally, the acquired data, e.g. vital signs data and EWS, may be validated and stored in the patient record in operation 63 before terminating the workflow in operation 65. This workflow 50 may be performed several times a day in order to ensure sufficient monitoring of the patient.

Figure 2:
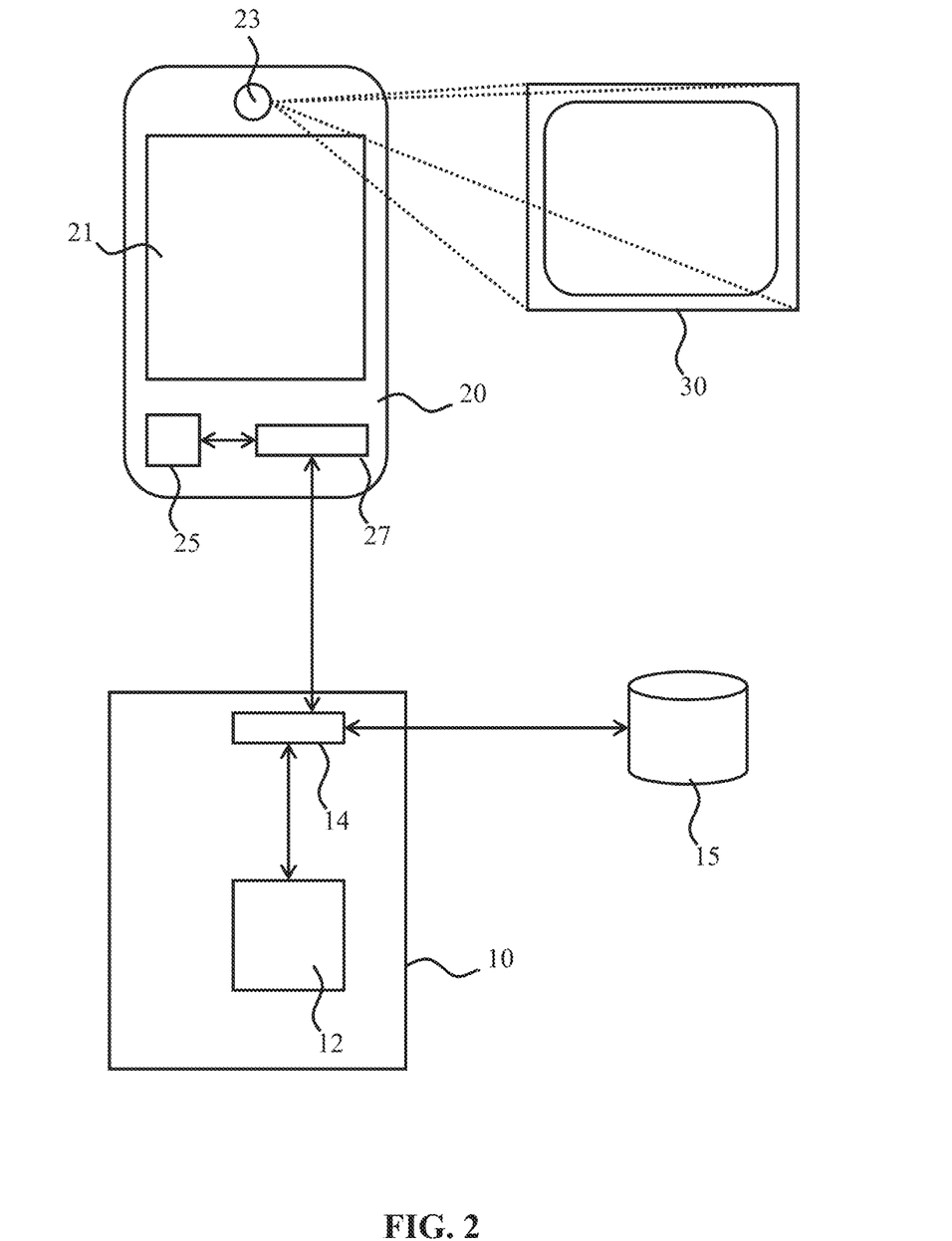
FIG. 2 schematically depicts a system for updating a patient record in accordance with an embodiment.

In accordance with embodiments of the present invention, the workflow 50 is adapted such that the healthcare professional is no longer required to manually input the vital signs data values of the patient, e.g. for the purpose of calculation of a score indicative of the actual physical state of the patient such as an EWS. Instead, the data required for such a calculation is obtained through the evaluation of an image of the display screen of the patient monitoring system on which the vital signs data of the patient is being displayed, with the vital signs data being extracted from this image such as through the use of optical character recognition algorithms. As such algorithms are well-known per se, the composition of such algorithms is not explained in further detail the sake of brevity only. An example infrastructure that may be used for this purpose is schematically depicted in FIG. 2. An electronic device 10 comprises a processor arrangement 12 and a data communication interface 14 under control of the processor arrangement 12. The electronic device 10 typically is communicatively coupled to a database 15 of patient records and any other database, e.g. through the data communication interface 14, which patient records typically comprise patient records of the patients within the clinical care environment in which the healthcare professionals operate, such as a hospital or the like.

The electronic device 10 may further be communicatively coupled to the electronic client device 20 to be used by the healthcare professional as previously explained. The electronic client device 20 may comprise a display screen 21, one or more cameras 23, a processor arrangement 25 and a data communication interface 27. The display screen 21, one or more cameras 23 and the data communication interface 27 are typically controlled by the processor arrangement 25. The electronic client device 20 typically stores a computer program such as the aforementioned app in a data storage device (not shown) such as a memory or the like. In some embodiments the data storage device can also include a database suitable for image storing. As will be further explained below, the electronic client device 20 is typically used by its user, e.g. the appropriate healthcare professional, to capture an image of the display screen 30 of the patient monitoring system on which the vital signs data values of the patient as captured by the patient monitoring system are displayed.

In the context of the present application, where reference is made to a processor arrangement, it should be understood that this is to include a single processor as well as a group of processors working together. In case of a single processor, such a processor may contain any suitable number of processor cores, e.g. one or more of such cores. Where reference is made to a data communication interface, it should be understood that this may be a wireless interface as well as a wired interface. In case of a wireless interface, the wireless data communication interface may deploy any suitable number of wireless communication protocols, such as for example one or more of WiFi, Bluetooth, and so on. In case of an electronic device being equipped to handle multiple communication protocols, it will be immediately understood by the skilled person that the electronic device may comprise multiple data communication interfaces dedicated to a particular one of these communication protocols. Where reference is made to a display screen, it should be understood that this may be any suitable type of display screen such as a CRT screen, LCD screen, LED screen, plasma screen, and so on. Such a screen may be a monochromatic screen, a colour screen, and so on.

In the context of the present application, where reference is made to a patient monitoring system it should be understood that this refers to any number of devices arranged to monitor one or more vital signs of a patient. Non-limiting examples of such patient monitoring systems include vital signs monitors, heart rate monitors, digital thermometers, blood glucose monitors, and so on.

In the context of the present application, where reference is made to a captured image it should be understood that such an image is typically captured in digital form, i.e. as a (pixelated) digital image. Moreover, as explained in more detail elsewhere, such an image may be a single image or a stream or temporal sequence of images, e.g. a video stream or the like.

It is furthermore noted that although FIG. 2 depicts an electronic device 10 and an electronic client device 20, it should be understood that it is equally feasible that the various aspects of the computer-implemented methods of the present invention to be described in more detail below may be implemented on a single electronic device such as the electronic client device 20, in which case the electronic device 10 may be omitted with the electronic client device 20 directly interfacing with the database 50 of patient records.

Figure 3:
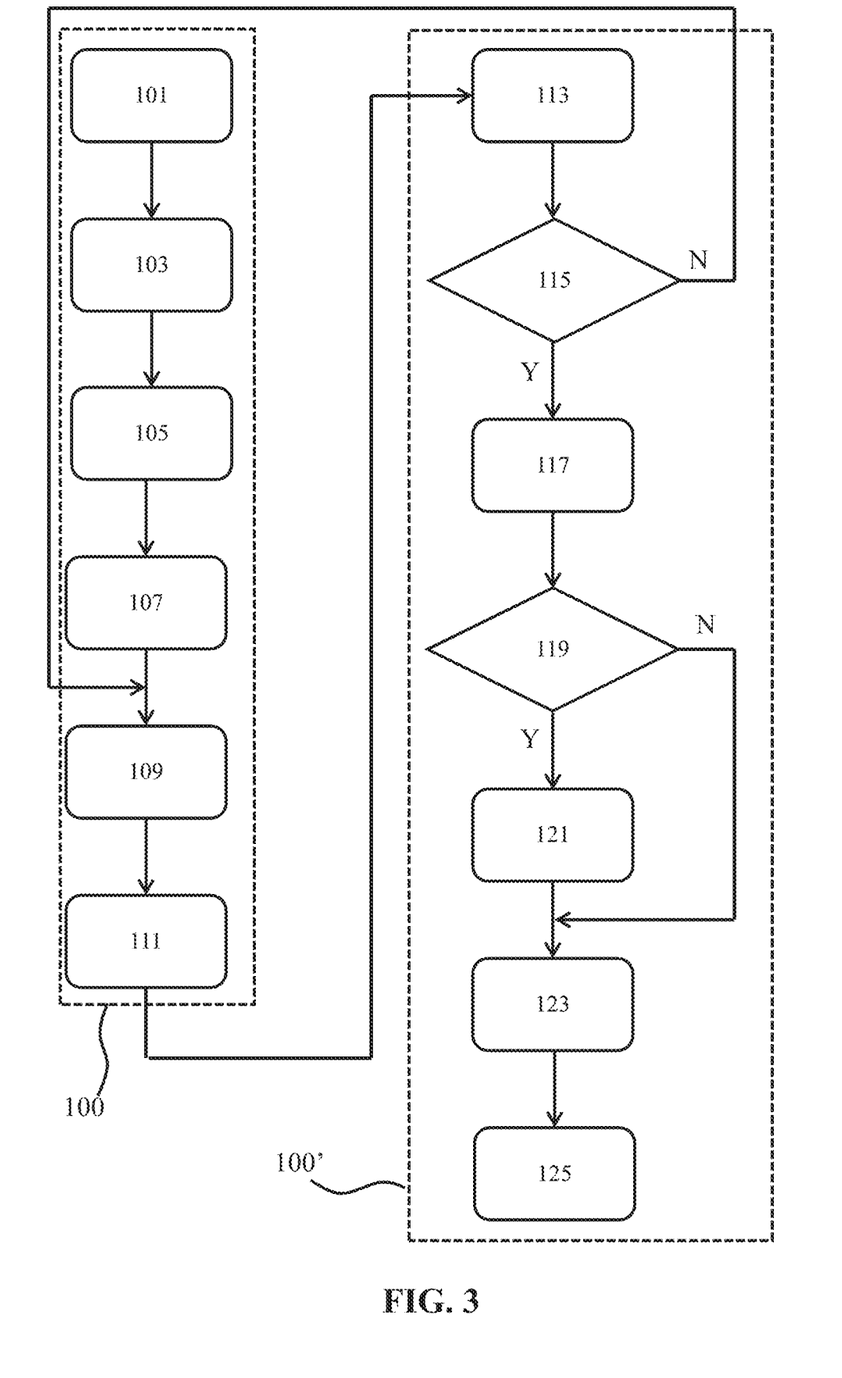
FIG. 3 schematically depicts a view of a patient monitor through a camera of an electronic client device according to an embodiment.

The operation of the electronic client device 20 and, if present, the electronic device 10 will be explained in more detail with the aid of FIG. 3-7. FIG. 3 depicts two distinct computer-implemented methods 100 and 100', i.e. methods to be performed by an electronic device comprising a processor arrangement such as the electronic device 10 or the electronic client device 20. In an embodiment, the computer-implemented method 100 is performed on the electronic client device 20 and the computer-implemented method 100' is performed on the electronic device 10 although in alternative embodiments at least some of the operations of the computer-implemented method 100' are performed on the electronic client device 20 instead. In a particular embodiment, all the operations of the computer-implemented method 100' are performed on the electronic client device 20, in which case the electronic device 10 may not be present or may be unused. The computer-implemented methods 100 and 100' may form part of the functionality of a software product such as an app installed on the electronic client device 20 and/or the electronic device 10. In a particular embodiment, at least the computer-implemented method 100 and optionally also the computer-implemented method 100' forms part of a patient monitoring app through which a healthcare professional can access the patient records (i.e. medical records) of patients in his or her care for evaluation and/or updating purposes as previously explained.

Figure 4:
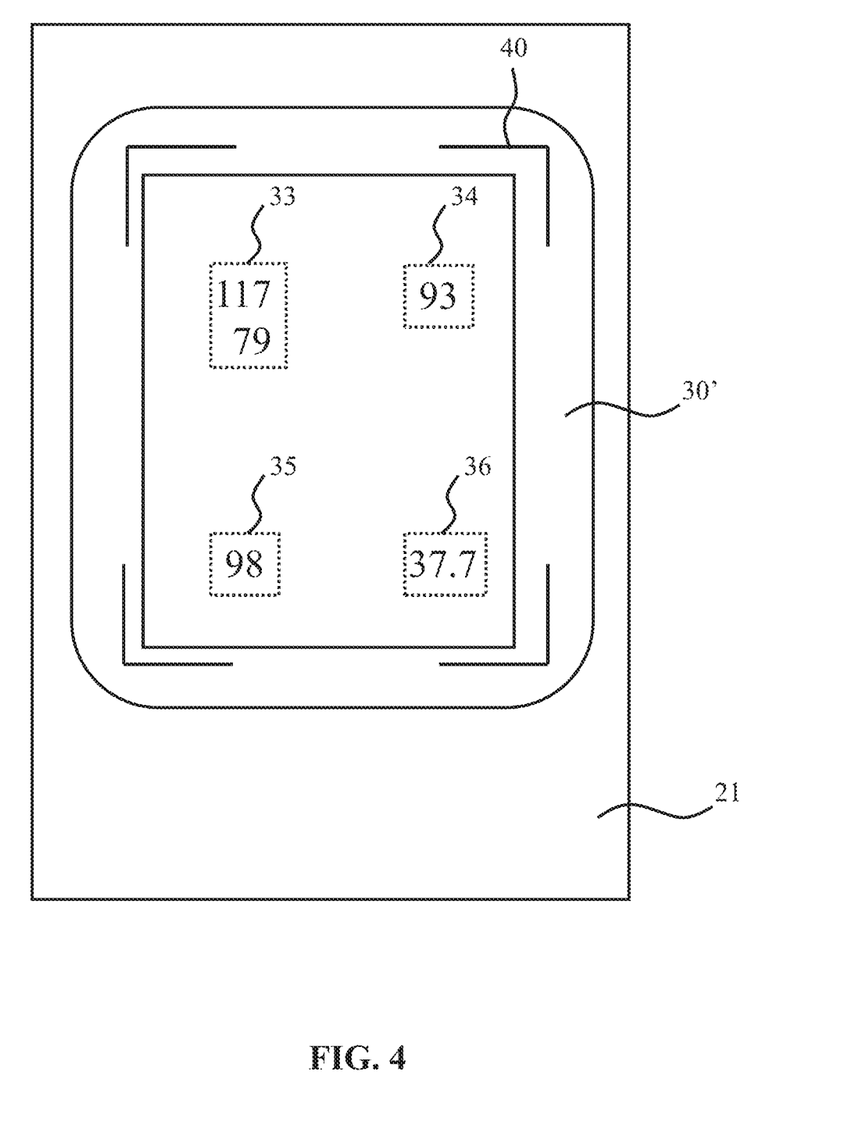
FIG. 4 schematically depicts a view of a patient monitor through a camera of an electronic client device according to another embodiment.

The computer-implemented method 100 is concerned with capturing an image of the display screen of the patient monitoring system through which the vital signs of the patient are acquired, i.e. capturing one or more of such images. The method 100 starts in 101 after which in operation 103 the processor arrangement 25 receives the identification information of the healthcare professional, e.g. a scan of his or her badge or the like or manually provided identification information, after which in operation 105 identification information for the patient is received, e.g. in the form of a scanned bracelet of wrist band or the like, based on which the patient record of the patient may be retrieved from the database 15. In the operation 107, the processor arrangement 25 overlays the display screen 21 of the electronic client device 20 with a mask corresponding to the relevant area of the display screen 30 of the patient monitoring system for acquiring the patient's vital signs. This is schematically depicted in FIG. 4, in which the mask 40 overlays a view 30' on the display screen 21 of the electronic client device 20 of the display screen 30 of the monitoring system for acquiring the patient's vital signs onto which the values 33-36 of these actual vital signs are being displayed. The view 30' of the display screen 30 of the monitoring system for acquiring the patient's vital signs onto which the values 33-36 of these actual vital signs are being displayed is typically obtained by the healthcare professional aiming the camera 23 of the electronic client device 20 at the display screen 30. The mask 40 is typically provided such that the healthcare professional can align the view through the camera 23 such that the area of the display screen 30 lies within the mask 40, thereby ensuring that upon capturing a photographic image of the view 30', all vital signs data values of interest as displayed on the display screen 30 are captured in the photographic image corresponding to the view 30'.

Figure 5:
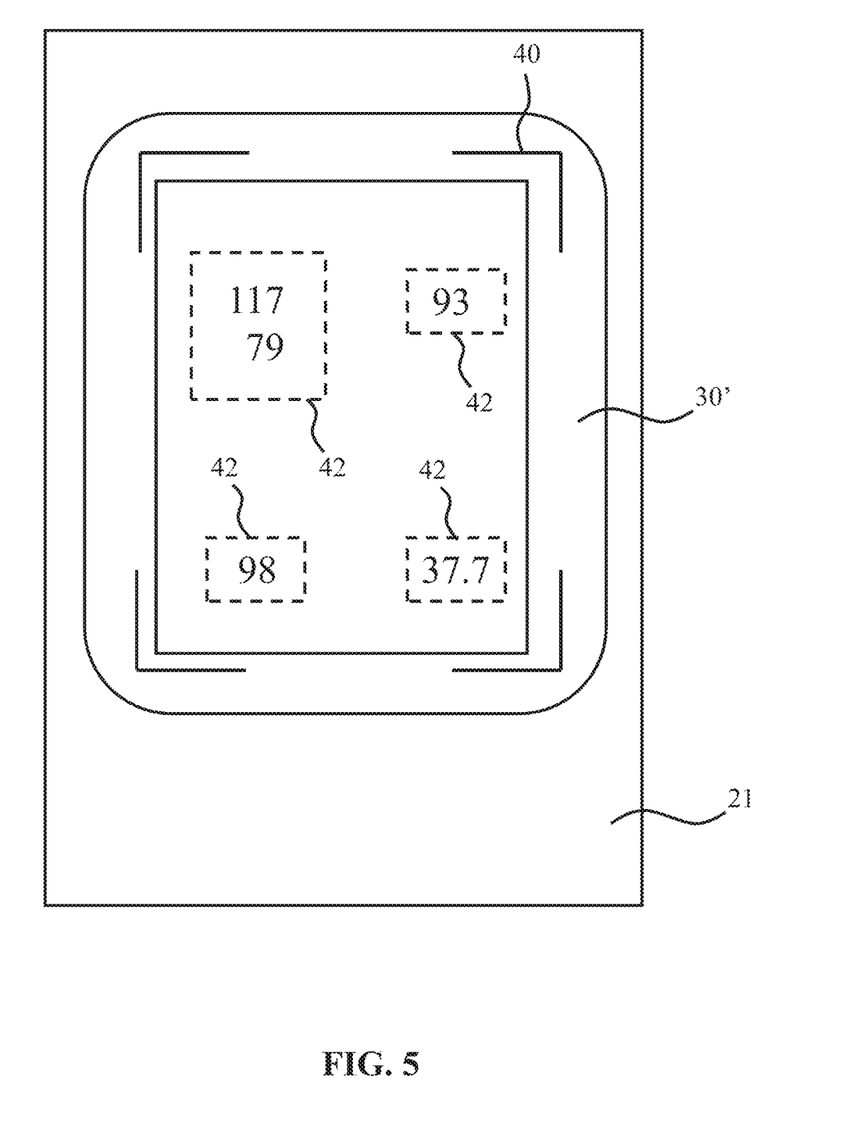
FIG. 5 schematically depicts vital signs data acquired with patient monitor displayed on a display screen of an electronic client device.

In a further refinement as schematically depicted in FIG. 5, the mask 40 may comprise one or more visible sectors 42, which may be aligned with the respective vital signs data values 33-36 in the view 30' of the display screen 30 of the patient monitoring system.

This further ensures that all relevant vital signs data values for the patient are captured as well as ensures that the relevant vital signs data values are captured in an area of the view 30' in which the processor arrangement adapted to extract the vital signs data values from the image corresponding to the view 30' expects those data values.

The software program (app) may be equipped with a single mask 40, which is automatically selected in operation 107 for overlaying the view 30'. This for example is appropriate in a scenario in which the healthcare facility typically uses the same patient monitoring system for all patients in that facility, such that a single mask 40 may be used to capture an image of the respective display screens of the different patient monitoring systems, given that all these screens have the same layout and dimensions. However, in an alternative scenario the healthcare facility utilizes a plurality of different types of patient monitoring systems in which different patient monitoring systems may have different types of display screens, e.g. display screens with different dimensions, display screens displaying different types of vital signs information, and so on. In such a scenario, the software program may be equipped with a library of masks 40, with each mask in the library corresponding to a display screen layout of a particular patient monitoring system such that upon trying to capture the vital signs information on such a display screen, the user (healthcare professional) of the electronic client device 20 may select the appropriate mask 40 from the library prior to capturing an image of the display screen 30' of the particular patient monitoring system with the aid of the selected mask 40. Alternatively, the electronic client device 20 may be adapted to automatically select the appropriate mask 40. This for example may be achieved by the user aiming a camera 23 of the electronic client device 20 at the display screen 30' or another part of the patient monitoring system, with the processor arrangement 25 evaluating this view and identifying the patient monitoring system therefrom, e.g. by comparing the view against a library of views of known patient monitoring systems such that the mask 40 corresponding to an identified patient monitoring system can be selected accordingly.

In operation 109, the processor arrangement 25 of the electronic client device 20 receives the user command to capture a photographic image of the actual view 30' through the camera 23, upon which the processor arrangement 25 captures this photographic image, e.g. by storing it in the data storage device (not shown) of the electronic client device 20, thereby obtaining a photographic image of the display screen 30 of the patient monitoring system containing the one or more vital signs data values of interest for the patient. Such a photographic image may form part of a sequence or stream of photographic images, e.g. a video stream or the like, in which at least some of the photographic images may be evaluated as explained in this application, e.g. to capture dynamic changes to the vital signs data values of the patient. In a particular example, a (video) camera may be continuously monitoring or capturing the display screen 30' of the patient monitoring system , such as to automatically capture the vital signs information of the patient over a prolonged period of time by capturing a stream of photographic images of the display screen 30' over this time period.

Figure 6:
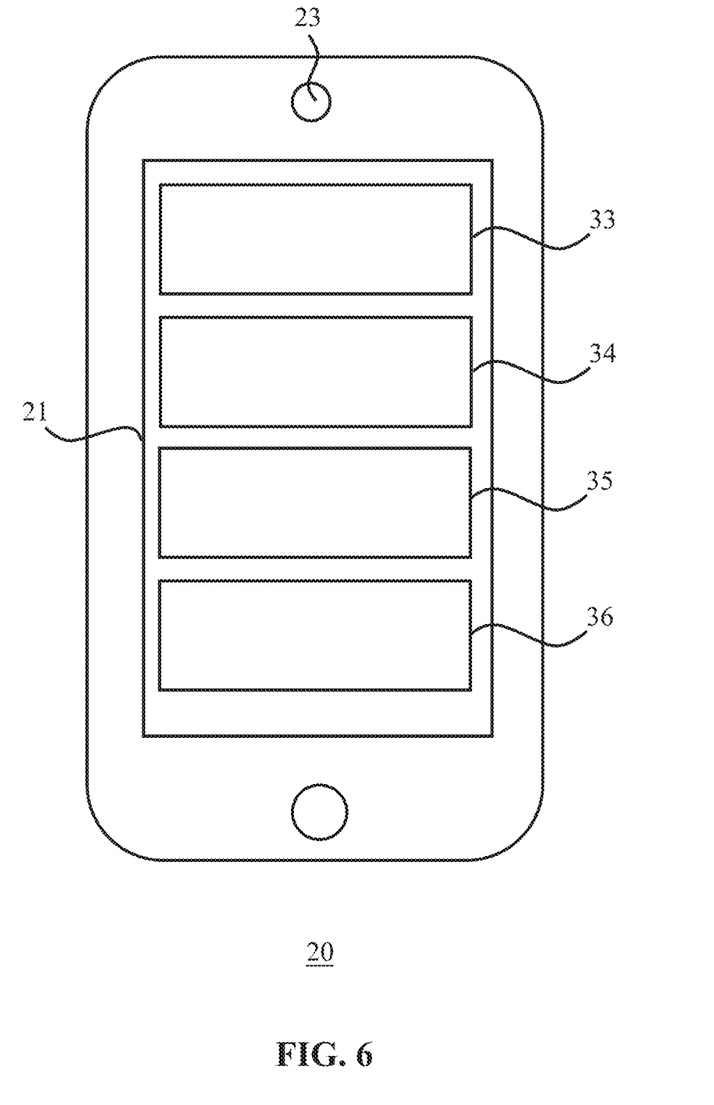
FIG. 6 schematically depicts vital signs data acquired with patient monitor and extracted from an image of the patient monitor displayed on a display screen of an electronic client device.

However, in some embodiments it may not be required to capture such a photographic image. For example, the electronic client device 20 may be configured with a further software program (app) for interfacing with the patient monitoring system, e.g. via a wireless link operated through the data communication interface 27, such that the one or more vital signs data values 33-36 for the patient as acquired with the patient monitoring system may be displayed directly onto the display screen 21 of the electronic client device 20 as schematically depicted in FIG. 6 (i.e. within the further software program). In such a scenario, an image in the form of screen capture (or screen print) of the information displayed on the display screen 21 may be produced instead, such that the vital signs data values may be extracted from the screen capture rather than from a photographic image of the display screen 30'.

Next, the at least one captured image containing the one or more vital signs data values is transferred in operation 111 to the processor arrangement adapted to extract those vital signs data values from the at least one image, e.g. using optical character recognition algorithms. This processor arrangement may be the processor arrangement 12 of the electronic device 10 or alternatively may be the processor arrangement 25 of the electronic client device 20, in which case the transfer operation 111 may be omitted.

In an embodiment in which the processor arrangement 25 is responsible in operation 113 for extracting the vital signs data values from the at least one captured (photographic) image, the processor arrangement 25 may further be adapted to attempt to recognize the vital signs data values of interest during the healthcare professional aiming the electronic client device 20 at the display screen 30 of the patient monitoring system, e.g. at a set frequency or continuously. In this manner, the healthcare professional operating the electronic client device 20 is provided with additional feedback by the processor arrangement 25 of whether the processor arrangement is capable of recognising the vital signs data values in the view 30' captured with the camera 23 of the electronic client device 20. The processor arrangement 25 may signal the successful recognition of one or more vital signs data values in this view in any suitable manner, for example by providing a visual indicator in the view 30' on the display screen 23 or by generating an audible or tactile indicator with the electronic client device 20. Such indicators may take any suitable form. The provision of generation of such an indicator signal to the healthcare professional that the photographic image corresponding to the actual view 30' of the display screen 30 of the patient monitoring system may be taken in the knowledge that the processor arrangement 25 can successfully extract or has successfully extracted the vital signs data values from this image. Alternatively, where the processor arrangement 12 of the electronic device 10 is responsible in operation for extracting the vital signs data values from the captured (photographic) image, such additional feedback cannot be provided, as the image has been captured prior to evaluation of the image by the processor arrangement 12.

The extraction of the one or more vital signs data values for the patient may be extracted from each captured image based on prior knowledge of the processor arrangement 12 or 25 of where in the image, i.e. which regions of interest within the image, comprise which data values. For example, the processor arrangement 12 or 25 may know in which region of interest a particular type of vital signs data value, e.g. a blood pressure value, is typically located. This may be achieved in any suitable manner. In a particular embodiment, a captured photographic image comprises metadata identifying the mask 40 (or the patient monitoring system corresponding to the mask 40) used to capture the photographic image such that the processor arrangement 12 or 25 can determine the layout of the display screen 30 captured in the photographic image from this metadata, e.g. by retrieving this layout from a library of layouts of display screens of patient monitoring systems in use within the clinical care environment.

Alternatively, the processor arrangement 12 or 25 may systematically evaluate a captured image to determine which vital signs data values are present in the captured image. This for example may be useful in a scenario in which the processor arrangement 12 or 25 does not have prior knowledge of where in the captured image the vital signs data values of interest can be found. In such a scenario, the processor arrangement 12 or 25 may attempt to recognize a vital signs data value in a particular region of the captured image and upon recognising this data value, attempt to match the data value to a particular type of vital sign, e.g. blood pressure, heart rate, body temperature, oxygen saturation, and so on by comparing the retrieved vital signs data value against typical expectation values of the data values of the various particular types of vital signs as well as by trying to identify a particular way in which the retrieved one or more vital signs data value are displayed. For example, a pair of values in close vicinity of each other and potentially separated by a return or a forward slash (/), e.g. 120/80, may be recognized by the processor arrangement 12 or 25 as a systolic and diastolic blood pressure value. A value of around 37 in close vicinity of a degree sign may be recognized as a body temperature, and so on.

Figure 7:
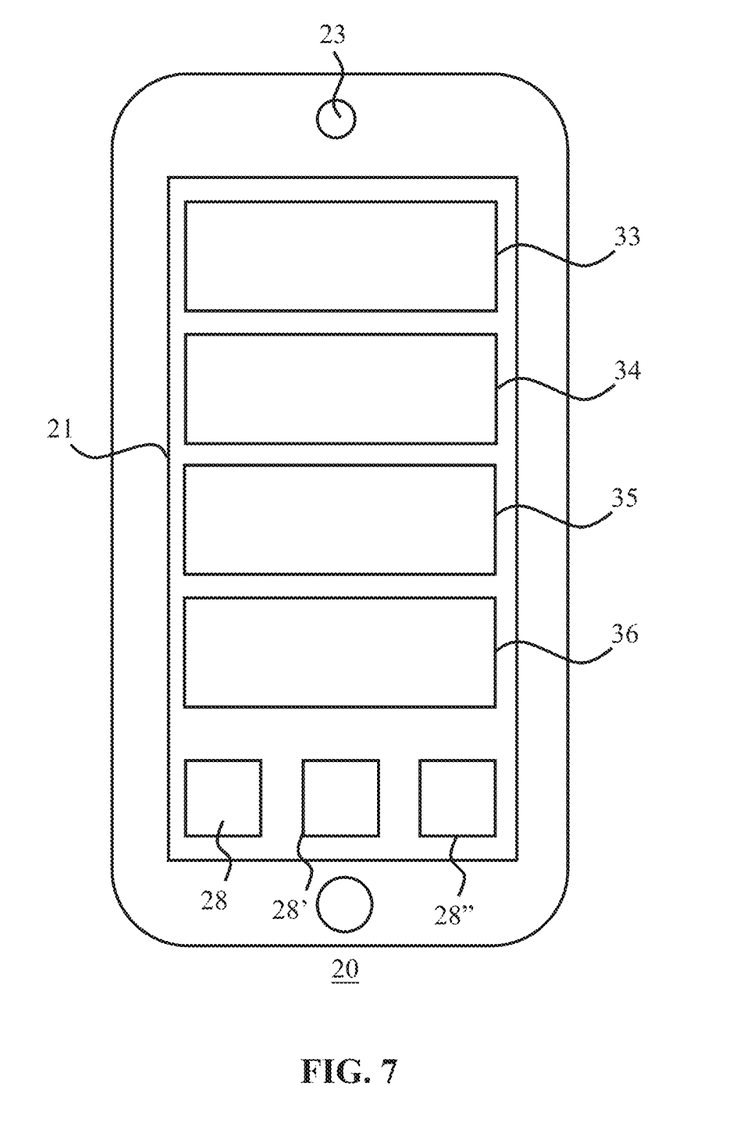
FIG. 7 schematically depicts a flowchart of respective computer-implemented methods according an example embodiment.

Upon extracting of the vital signs data values from the image in operation 113, the method 100' may proceed to operation 115 in which the extracted vital signs data values are to be verified by the user, e.g. by presenting the extracted vital signs data values on the display screen 23 of the electronic client device 20. For example, the processor arrangement 25 may receive the extracted vital signs data values from the processor arrangement 12 via data communication interfaces 14 and 27 in case the processor arrangement 12 was responsible for extracting the vital signs data values from the captured image. FIG. 7 schematically depicts an example embodiment of the display screen 23 displaying extracted vital signs data values 33-36 with one or more buttons 28 through which the user (i.e. the healthcare professional) can verify the extracted data values, e.g. by comparing them with the data values displayed on the display screen 30 of the patient monitoring system. For example, the one or more buttons 28 may allow the user to accept the extracted one or more vital signs data values, to accept and store the extracted one or more vital signs data values or to reject the extracted one or more vital signs data values. Of course, such verification functionality may take any suitable shape and is not limited to buttons 28 only. Furthermore, the verification functionality typically includes an option to accept as well as an option to reject the extracted one or more vital signs data values.

If the user of the electronic client device 20 rejects the extracted one or more vital signs data values, the process may optionally return to operation 109 in which the user may capture another (i.e. improved) image of the data screen 30 of the patient monitoring system. Alternatively, the user may decide to manually input the one or more vital signs data values of interest at this point. On the other end, if the user accepts the extracted one or more vital signs data values, the method 100' may proceed to operation 117 in which the processor arrangement 12 or 25 calculates the score indicative of the physical well-being of the patient, e.g. an EWS, based on the approved extracted one or more vital signs data values and, if provided, additional observations of the healthcare professional such as AVPU information for example. The processor arrangement 12 or 25 may evaluate the calculated score in operation 119 and generate a visible or audible alarm with the electronic client device 20 in operation 121 if the calculated score is indicative of poor or deteriorating health of the patient, e.g. a physical state requiring urgent medical care, such that healthcare professional is alerted to the fact that the patient may require additional medical care.

Otherwise, the method 100' proceeds directly to operation 123 in which the calculated score and/or the extracted one or more vital signs data values are stored in the patient record within the medical database 15 by the processor arrangement 12 or 25. At the same time, the captured image may be stored in the medical database 15 and linked to the stored calculated score and/or the extracted one or more vital signs data values such that at any point in time the calculated score and/or the extracted one or more vital signs data values may be scrutinized using the stored image of the display screen 30 onto which the one or more vital signs data values are displayed. Preferably, the identification information of the healthcare professional is also stored in the medical database 15 and linked to at least one of the stored image, the stored calculated score and/or the stored extracted one or more vital signs data values such that in case of such scrutinizing highlighting a problem with the stored data or score, e.g. because of inappropriate validation of the extracted vital signs data values, the responsible healthcare professional can be easily identified. The method 100'subsequently terminates in operation 125.

The above described embodiments of the methods 100 and 100' may be realized by computer readable program instructions embodied on a computer readable storage medium having, when executed on a processor arrangement 12 and/or 25, cause the processor arrangement to implement the method 100 and/or 100'. Any suitable computer readable storage medium may be used for this purpose, such as for example an optically readable medium such as a CD, DVD or Blu-Ray disc, a magnetically readable medium such as a hard disk, an electronic data storage device such as a memory stick or the like, and so on. The computer readable storage medium may be a medium that is accessible over a network such as the Internet, such that the computer readable program instructions may be accessed over the network. For example, the computer readable storage medium may be a network-attached storage device, a storage area network, cloud storage or the like. The computer readable storage medium may be an Internet-accessible service from which the computer readable program instructions may be obtained. In an embodiment, the electronic device 10 and/or the electronic client device 20 is adapted to retrieve the computer readable program instructions from such a computer readable storage medium and to create a new computer readable storage medium by storing the retrieved computer readable program instructions in a data storage arrangement (not shown), e.g. in a memory device or the like forming part of the data storage arrangement.

It shall be understood by the person skilled in the art that the medical database 15 and the database, wherein the image is stored, could be the same database or two separate ones with appropriate links between the patient records.

It should be noted that the above-mentioned embodiments illustrate rather than limit the invention, and that those skilled in the art will be able to design many alternative embodiments without departing from the scope of the appended claims. In the claims, any reference signs placed between parentheses shall not be construed as limiting the claim. The word "comprising" does not exclude the presence of elements or steps other than those listed in a claim. The word "a" or "an" preceding an element does not exclude the presence of a plurality of such elements. The invention can be implemented by means of hardware comprising several distinct elements. In the device claim enumerating several means, several of these means can be embodied by one and the same item of hardware. The mere fact that certain measures are recited in mutually different dependent claims does not indicate that a combination of these measures cannot be used to advantage.

The invention claimed is:

1. A computer-implemented method of updating a patient record in a medical database, the method comprising:
   receiving an image depicting a display screen of a patient monitoring system, wherein the image depicting the display screen of the patient monitoring system contains a depiction of displaying at least one vital signs data value of a patient;
   extracting a vital signs data value from the received image by evaluating at least one region of interest of the received image by applying a mask stored in a data storage, the at least one region of interest comprising the vital signs data value, wherein the mask is configured to align with the at least one region of interest of the display screen of the patient monitoring system;
   updating the patient record with the extracted vital signs data value; and
   storing the image in a database such that the image is associated with the updated patient record.

2. The computer-implemented method of claim 1, further comprising generating an indicator value of an actual physical state of the patient from the extracted vital signs data value and updating the patient record with the generated indicator value.

3. The computer-implemented method of claim 1, wherein the image is stored is the medical database.

4. The computer-implemented method of claim 1, further comprising:
   displaying the extracted vital signs data value on a display device to a user;
   receiving a verification command from the user; and
   updating the patient record with the extracted vital signs data value and storing the image in at least one of the medical database or the database in response to the received verification command.

5. The computer-implemented method of claim 1, wherein evaluating the image to extract the vital signs data value from a region of interest in the image comprises:
- identifying the region of interest comprising the vital signs data value in the image;
- extracting the vital signs data value from the identified region of interest;
- matching the extracted vital signs data value to a particular vital sign of the patient by comparing the vital signs data value against a library of expectation values of data values for different vital signs; and
- updating a vital signs record of a vital sign in the patient record matched to the extracted vital signs data value with the extracted vital signs data value.

6. The computer-implemented method of claim 1, wherein the image is at least one photographic image or a screen capture.

7. The computer-implemented method of claim 1, further comprising receiving identification information of a person responsible for generating the image and associating at least one of the stored at least one vital signs data value and the stored image with the received identification information.

8. A non-transitory computer readable medium storing instructions that, when executed by one or more processors, cause the one or more processors to:
- receive an image depicting a display screen of a patient monitoring system, wherein the image depicting the display screen of the patient monitoring system contains a depiction of displaying at least one vital signs data value of a patient;
- extract a vital signs data value from the received image by evaluating at least one region of interest of the received image by applying a mask stored in a data storage, the at least one region of interest comprising the vital signs data value, wherein the mask is configured to align with the at least one region of interest of the display screen of the patient monitoring system;
- update a patient record with the extracted vital signs data value; and
- store the image in a database such that the image is associated with the updated patient record.

9. A system for updating a patient record in a medical database, the system comprising:
- one or more processors;
- a camera communicatively coupled to the one or more processors;
- a display screen of a patient monitoring system, the display screen communicatively coupled to the one or more processors;
- a data storage comprising a mask configured to align with a region of interest of the display screen of the patient monitoring system; and
- a memory communicatively coupled to the one or more processors, the memory comprising instructions for:
  - receiving an image depicting the display screen of the patient monitoring system, wherein the image depicting the display screen of the patient monitoring system contains a depiction of displaying at least one vital signs data value of a patient;
  - extracting a vital signs data value from the received image by evaluating at least one region of interest of the received image by applying the mask from the data storage, the at least one region of interest comprising the vital signs data value;
  - updating the patient record with the extracted vital signs data value; and
  - storing the image in a database such that the image is associated with the updated patient record.

10. The non-transitory computer readable medium of claim 8, wherein the instructions, when executed by the one or more processors, further cause the one or more processors to:
- generate an indicator value of an actual physical state of the patient from the extracted vital signs data value and updating the patient record with the generated indicator value.

11. The non-transitory computer readable medium of claim 8, wherein the image is stored is the medical database.

12. The non-transitory computer readable medium of claim 8, wherein the instructions, when executed by the one or more processors, further cause the one or more processors to:
- display the extracted vital signs data value on a display device to a user;
- receive a verification command from the user; and
- update the patient record with the extracted vital signs data value and storing the image in at least one of the medical database or the database in response to the received verification command.

13. The non-transitory computer readable medium of claim 8, wherein, to evaluate the image to extract the vital signs data value from a region of interest in the image, the instructions, when executed by the one or more processors, further cause the one or more processors to:
- identify the region of interest comprising the vital signs data value in the image;
- extract the vital signs data value from the identified region of interest;
- match the extracted vital signs data value to a particular vital sign of the patient by comparing the vital signs data value against a library of expectation values of data values for different vital signs; and
- update a vital signs record of a vital sign in the patient record matched to the extracted vital signs data value with the extracted vital signs data value.

14. The non-transitory computer readable medium of claim 8, wherein the image is at least one photographic image or a screen capture.

15. The non-transitory computer readable medium of claim 8, further comprising receiving identification information of a person responsible for generating the image and associating at least one of the at least one vital signs data value and the stored image with the received identification information.

16. The system of claim 9, wherein the memory further comprises instructions for:
- generating an indicator value of an actual physical state of the patient from the extracted vital signs data value and updating the patient record with the generated indicator value.

17. The system of claim 9, wherein the image is stored is the medical database.

18. The system of claim 9, wherein the memory further comprises instructions for:
- displaying the extracted vital signs data value on a display device to a user;
- receiving a verification command from the user; and
- updating the patient record with the extracted vital signs data value and storing the image in at least one of the medical database or the database in response to the received verification command.

19. The system of claim 9, wherein, to evaluate the image to extract the vital signs data value from a region of interest in the image, the memory further comprises instructions for:
- identifying the region of interest comprising the vital signs data value in the image;
- extracting the vital signs data value from the identified region of interest;
- matching the extracted vital signs data value to a particular vital sign of the patient by comparing the vital signs data value against a library of expectation values of data values for different vital signs; and
- updating a vital signs record of a vital sign in the patient record matched to the extracted vital signs data value with the extracted vital signs data value.

20. The system of claim 9, wherein the image is at least one photographic image or a screen capture.

* * * * *